(12) United States Patent
Hassan et al.

(10) Patent No.: US 7,652,175 B2
(45) Date of Patent: Jan. 26, 2010

(54) HIGH SHEAR PROCESS FOR THE PRODUCTION OF ACETALDEHYDE

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 0 days.

(21) Appl. No.: 12/136,320

(22) Filed: Jun. 10, 2008

(65) Prior Publication Data

US 2009/0005605 A1  Jan. 1, 2009

Related U.S. Application Data

(60) Provisional application No. 60/946,470, filed on Jun. 27, 2007.

(51) Int. Cl.
*C07C 45/34* (2006.01)
(52) U.S. Cl. ..................................................... 568/476
(58) Field of Classification Search .................. 568/476
See application file for complete search history.

(56) References Cited

U.S. PATENT DOCUMENTS

| 3,869,518 | A | 3/1975 | Sze et al. |
| 5,506,363 | A | 4/1996 | Grate et al. |
| 5,679,870 | A | 10/1997 | Tustin et al. |
| 5,710,342 | A | 1/1998 | Imre et al. |
| 6,331,314 | B1 | 12/2001 | Klinksiek et al. |
| 6,866,411 | B1 | 3/2005 | Stezler et al. |

*Primary Examiner*—Sikarl A Witherspoon
(74) *Attorney, Agent, or Firm*—Conley Rose, P.C.

(57) ABSTRACT

A method of use for a high shear device incorporated into a process or system for the production of acetaldehyde from ethylene as a reactor device is shown to be capable of decreasing mass transfer limitations, by forming a feed stream emulsion, and thereby enhancing the acetaldehyde production process in the system.

11 Claims, 2 Drawing Sheets

HIGH SHEAR PROCESS FOR THE PRODUCTION OF ACETALDEHYDE

CROSS-REFERENCE TO RELATED APPLICATIONS

This application claims the benefit under 35 U.S.C. § 119(e) of U.S. Provisional Patent Application No. 60/946,470 filed Jun. 27, 2007, the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of acetaldehyde, and more particularly to apparatus and methods for catalytically converting ethylene to acetaldehyde. More specifically, the disclosure relates to the reduction of mass transfer limitations in apparatus and methods for catalytically converting ethylene to acetaldehyde.

2. Background of the Invention

Acetaldehyde is an important, basic material for production of many organic substances, and its derivatives including many industrially significant products such as acetic acid, acetic esters, and related compounds. Important processes for the commercial production of acetaldehyde have included the acetylene hydration process, the ethanol dehydration process, and the ethylene direct oxidation process. Of these processes, acetylene hydration and ethanol dehydration are no longer used, because large amounts of byproducts are formed, primarily due to the relatively severe reaction conditions required.

In contrast to the above processes, the so-called Wacker's process for producing acetaldehyde employs relatively mild reaction conditions. In Wacker's process, ethylene is used as raw feed material and palladium chloride ($Pd(2)Cl_2$)-cupric chloride ($Cu(2)Cl_2$) is used as a catalyst. Because oxygen has a low solubility in water, conventional practice has been to increase the amount of oxygen dissolved by carrying out the reaction under pressure and temperature conditions of about 10 Kg/cm2 and 100° C. However, when excess dissolved oxygen is released into the gas phase and mixes with ethylene, explosive mixtures can result.

Accordingly, there is a need in the industry for improved processes for the production of acetaldehyde whereby production rates are increased, explosion hazards are reduced, and milder reaction conditions, such as lower temperature and pressure, are commercially feasible.

SUMMARY OF THE INVENTION

A high shear system and process for accelerating acetaldehyde production is disclosed. The high shear process reduces mass transfer limitations, thereby enhancing the effective reaction rate and allowing reactor operation at reduced temperature and pressure, with reduced contact time and/or an increase in product yield. In accordance with certain embodiments of the present disclosure, a process is provided that makes possible an increase in the rate of production of acetaldehyde, by providing for more optimal time, temperature, and pressure conditions than are conventionally used.

In an embodiment described in the present disclosure, a process employs a high shear mechanical reactor to provide enhanced time, temperature, and pressure reaction conditions resulting in accelerated chemical reactions between multiphase reactants. Further, a process disclosed in an embodiment described herein comprises the use of a pressurized high shear device to provide for the production of acetaldehyde without the need for high volume, high pressure reactors.

These and other embodiments, features and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Overview

Figure 1:
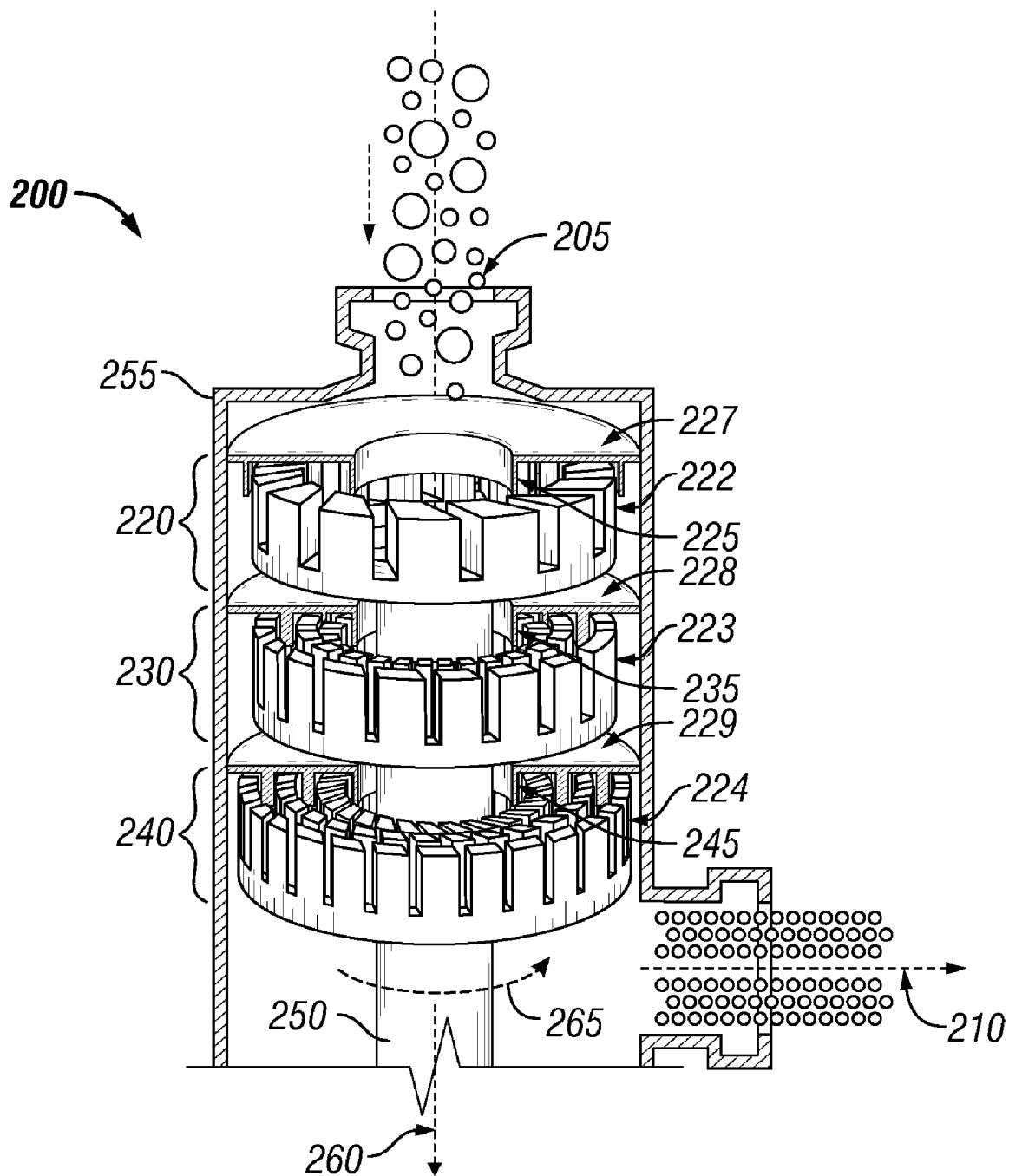
FIG. 1 is a cross-sectional diagram of a high shear device for the production of acetaldehyde.

An improved process and system for the production of acetaldehyde employs an external or in-line high shear device. The high shear device is a mechanical reactor, mixer, or mill to provide rapid contact and mixing of chemical reactants in a controlled environment in the device. The high shear device reduces the mass transfer limitations on the reaction and thus increases the overall reaction rate.

Chemical reactions involving liquids, gases, solids, and catalysts rely on the laws of kinetics that involve time, temperature, and pressure to define the rate of reactions. In cases where it is desirable to react two or more raw materials of different phases (e.g. solid and liquid; liquid and gas; solid, liquid, and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants.

In conventional reactors, the contact time for the reactants and/or catalyst is often controlled by mixing, which provides contact between two or more reactants involved in a chemical reaction. A reactor assembly that comprises a high shear device prior to reactant introduction, reduces the mass transfer limitations and thereby allows the reaction to more closely approach the intrinsic kinetic rate. When effective reaction rates are accelerated, residence times may be decreased, thereby increasing the throughput obtainable. Alternatively, where the present yield is acceptable, decreasing the required residence time allows for the use of less severe temperatures and/or pressures than conventional processes.

High Shear Device

High shear devices (HSD) such as a high shear mixer, or high shear mill, are generally divided into classes based upon their ability to mix fluids. Mixing is the process of reducing the size of inhomogeneous species, bubbles, or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle, globule, or bubble sizes in the range of 0 to 50 µm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy-high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m³. In embodiments, the energy expenditure is in the range of from about 3000 W/m³ to about 7500 W/m³. The shear rate generated in a high shear device may be greater than 20,000 s⁻¹. In embodiments, the shear rate generated is in the range of from 20,000 s⁻¹ to 100,000 s⁻¹.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec)=π·D·n, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, 2πR, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1034 MPa (150,000 psi) and elevated temperatures at the tip of the shear mixer are produced during operation. The local pressure further depends on the tip speed, fluid viscosity, and the rotor-stator gap during operation.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feed stream 205 comprises a gas, or globule size, if feed stream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the average bubble size is in the range from about 1.0 µm to about 0.1 µm. Alternatively, the average bubble size is less than about 400 nm (0.4 µm) and most preferably less than about 100 nm (0.1 µm).

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam.

Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants. Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," Current Science 91 (No. 1): 35-46 (2006). The high shear mixing device of certain embodiments of the present system and methods is operated under what is believed to be cavitation conditions effective to dissociate the ethylene and water into free radicals exposed to catalysts and hydrochloric acid for the oxidation of the ethylene to form the aldehyde product.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300-700 l/h (depending on generator), a tip speed of from 9.4-41 m/s (about 1850 ft/min to about 8070 ft/min). Several alternative models are available having various inlet/outlet connections, horsepower, nominal tip speeds, output rpm, and nominal flow rate.

Description of High Shear Acetaldehyde Production Process and System

Figure 2:
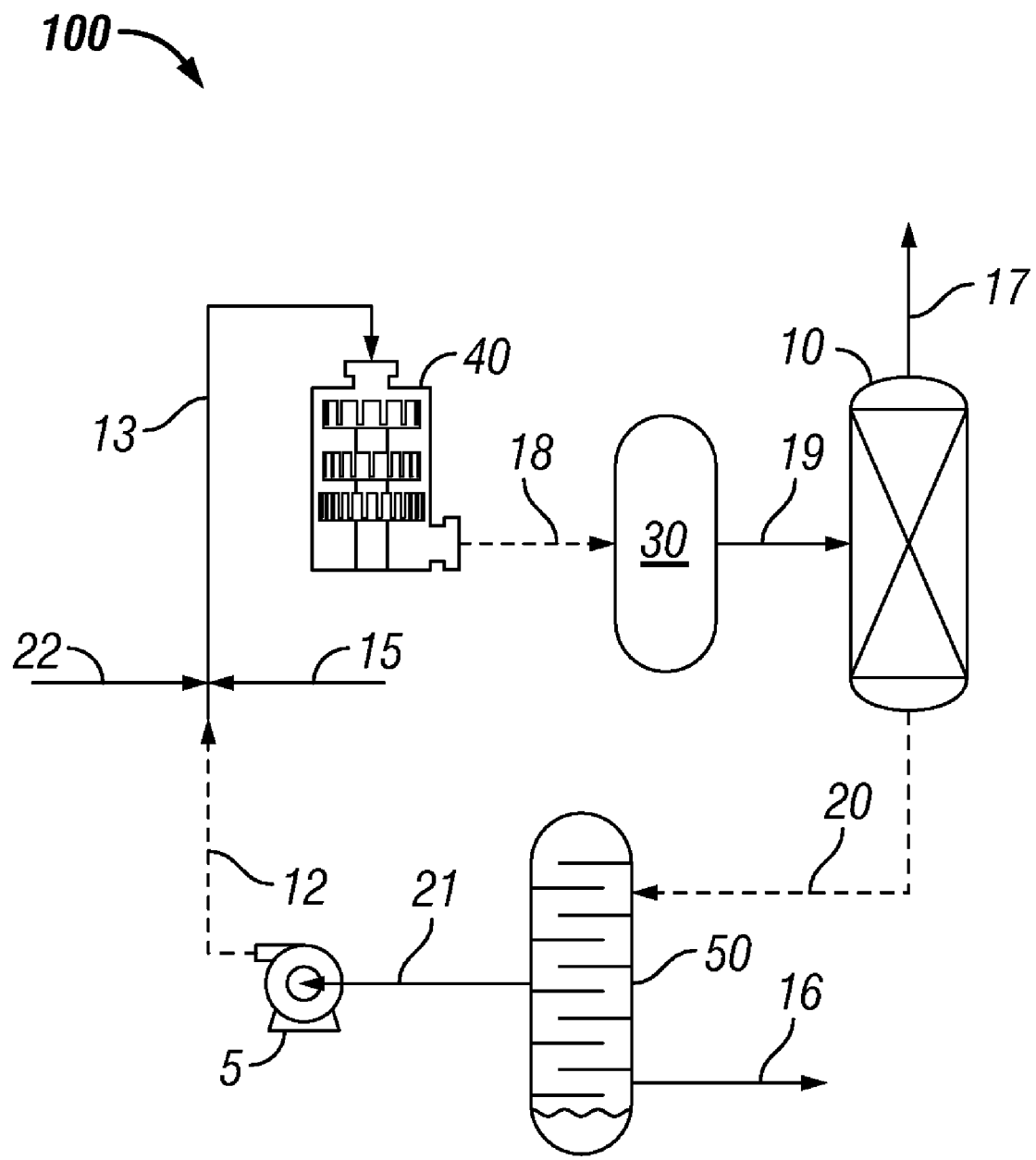
FIG. 2 is a process flow diagram according to an embodiment of the present disclosure comprising a high shear process for the production of acetaldehyde.

The high shear acetaldehyde production process and system of the present disclosure will now be described in relation to FIG. 2 which is a representative process flow diagram of a high shear system 100 for the production of acetaldehyde comprising high shear device 40. Continuous oxidation of ethylene has been made possible by a redox system. According to the process, a composite catalyst obtained by dissolving Pd(2)Cl$_2$ and Cu(2)Cl$_2$ as catalysts in hydrochloric acid solution (pH~2.0) is employed. Ethylene is oxidized with divalent palladium Pd(2) and water to form acetaldehyde (CH$_3$CHO). The reaction is expressed by the following equation wherein water participates in the reaction:

$$CH_2=CH_2+Pd(2)Cl_2+H_2O \rightarrow CH_3CHO+Pd(0)+2HCl \quad (1)$$

As seen from Equation (1), Pd(2) is reduced to metal palladium Pd(0) which precipitates. This is prevented by making Cu(2)Cl2 coexistent in a large amount, and at the same time, Pd(0) is oxidized into Pd(2) for regeneration according to the following equation:

$$Pd(0)+2Cu(2)Cl_2 \rightarrow Pd(2)Cl_2+2Cu(1)Cl \quad (2)$$

Slightly soluble Cu(1)Cl is oxygen-oxidized in the copresence of HCl and returned to Cu(2)Cl$_2$ according to the following equation:

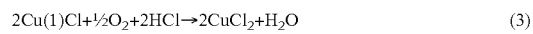

$$2Cu(1)Cl+\tfrac{1}{2}O_2+2HCl \rightarrow 2CuCl_2+H_2O \quad (3)$$

By employing a redox system of Pd(2)/Pd(0) and Cu(2)/Cu (1), continuous oxidation of ethylene is possible. Since oxygen has a low solubility in water, it has conventionally been necessary for accelerating the reaction by increasing its amount dissolved, to carry out the reaction under pressure and heating conditions as mentioned herein.

The high shear acetaldehyde production process and system create an oxygen, or other gaseous oxidant, emulsion in the aqueous feed stream including ethylene prior to introduction to an acetaldehyde reactor. FIG. 2 illustrates the basic components of a representative high shear acetaldehyde production system in which the process is carried out. These components comprise high shear device 40, reactor 10, and pump 5. The pump 5 increases the pressure of the pump inlet aqueous stream 21 to greater than about 203 kPA (2 atm), alternatively, greater than about 304 kPA (3 atm). Preferably, all contact parts of pump 5 comprise stainless steel. Pump 5 may be any suitable pump, for example, a Roper Type 1 gear pump, Roper Pump Company (Commerce Ga.) or Dayton Pressure Booster Pump Model 2P372E, Dayton Electric Co (Niles, Ill.). Pump 5 is used to provide a controlled flow throughout high shear device 40 and high shear acetaldehyde production system 100.

Pump 5 builds pressure and feeds high shear device 40. After pumping, the pressurized acetic acid comprises exit stream 12 is mixed with oxidant dispersible stream 22, which serves to create a mixture of the oxidant and the exit stream 12. Dispersible reactant stream 22 comprises an oxidant to be dispersed in aqueous solution for the production of acetaldehyde from ethylene. Further the reactant 15, comprising ethylene, is mixed with dispersible gas stream 22. The combined pressurized exit stream 12, oxidant dispersible stream 22 and reactant stream 15 comprise the high shear inlet stream 13. High shear device 40 is positioned between pump 5 and reactor 10. The dispersible oxidant stream 22 and exit stream 12 are injected into high shear inlet stream 13, which feeds high sheer device 40. High shear device 40 produces an emulsion of the oxidant gas bubbles in the aqueous discharge stream 18. In this way, high shear system 100 combines high shear with pressure to enhance reactant intimate mixing prior to introduction to the reactor.

High shear device discharge stream 18 is passed to heater 30. Heater outlet stream 19 is introduced to reactor 10. Reactor discharge stream 20 enters surge tank 50 and acetaldehyde may be removed from high shear system 100 via product stream 16. Reaction medium may be recycled, by transporting the reactor medium from reactor discharge 20, to pump input stream 21, to pump 5 and returning to high shear mixer 40. In certain embodiments, the reaction medium is recycled through pump 5 to pump the reaction medium to an increased pressure.

In embodiments, dispersible reactant stream 22 comprises oxygen and/or enriched air plus $H_2O$ as the oxidant. Atmospheric air may also be utilized, however, the additional capital costs associated with handling larger amounts of inert gases (air is approximately 78% nitrogen) usually make use of air less attractive that sources with higher oxygen content.

Reactor 10 is any type of reactor in which the above-described reactions (1)-(3) can be carried out. Reactor 10 may be, for example, a fixed bed reactor comprising a fixed bed catalyst. The redox reaction carried out by high shear system 100 is a catalytic reaction involving a dissolved $Pd(2)Cl_2$ catalyst and $Cu(2)Cl_2$ catalyst in hydrochloric acid solution. Reactor 10 may comprise a fixed bed of, for example, palladium chloride/cupric chloride based catalyst. When fixed bed catalyst is utilized, the reactor becomes the main location for the hydrogenation reaction to occur due to the presence of catalyst and its effect on the rate of oxidation.

Oxidation reactions will occur whenever suitable time temperature and pressure conditions exist. In this sense oxidation could occur at any point in the high shear system 100 if temperature and pressure conditions are suitable. In certain embodiments, a slurry bed catalyst may be used in conjunction with a fluidized bed reactor. Where a slurry based catalyst is utilized, reaction is more likely to occur at points outside the reactor 10. Nonetheless a discrete reactor is often desirable to allow for increased residence time, agitation and heating and/or cooling.

If a catalyst is used to promote the partial oxidation reaction, it may be introduced into the reactor 10 as an aqueous or non-aqueous slurry or stream. In certain instances, the catalyst is added continuously to reactor 10, or alternatively, to inlet stream 13. Alternatively, or additionally, catalyst may be added elsewhere in the system 100. For example, where slurry catalyst is utilized, the catalyst may also be introduced in pump inlet stream 21 or pump exit stream 12. In fixed bed applications, catalyst comprises a fixed bed catalyst within the reactor 10.

As discussed in detail above, high shear device 40 is a mechanical device that utilizes, for example, a rotor stator mixing head with a fixed gap between the stator and rotor. Dispersible oxidant stream 22 and liquid pump outlet stream 12 are introduced separately or as mixed stream 13 into the inlet of high shear device 40. Mixing results in dispersion of oxidant in micron or sub micron particles. Therefore, high shear device discharge stream 18 comprises an emulsion of micron and/or submicron-sized gas bubbles, as discussed hereinabove. High shear device discharge stream 18 is introduced into reactor 10 as reactor recycle stream 19 which is high shear device discharge stream 18 which optionally has undergone further processing prior to recycle to reactor 10. For example, high shear device discharge stream 18 may be heated in a heater 30 prior to entering reactor 10 as inlet stream 19. Reactor inlet stream 19 enters reactor 10 wherein acetaldehyde production continues.

In reactor 10, acetaldehyde is produced via redox reactions in Equations (1)-(3) above. Liquid acetaldehyde exits via product stream 16. In embodiments, reactor discharge stream 20 does not enter surge tank 50. In embodiments, the surge tank 50 comprises an optional heat exchanger. The use of external heating and/or cooling heat transfer devices is also contemplated. Suitable locations for external heat transfer devices would be between the reactor 10 and the surge tank 50, between the surge tank 10 and the pump 5; between the pump 5 and the high shear device 40 or between the high shear device 40 and the reactor 10. There are many types of heat transfer devices that may be suitable and are known to those experienced in the art. Such exchangers might include shell and tube, plate, and coil heat exchangers. Use of the disclosed process comprising reactant mixing via high shear device 40 allows use of lower temperature and/or pressure in reactor 10 than previously enabled. The method comprises incorporating high shear device 40 into an established process thereby reducing the operating temperature and/or pressure of the reaction in high shear device 40 and/or enabling the increase in production, for example greater throughput, from a process operated without high shear device 40. The reactor 10 is operated at near atmospheric pressure and acetaldehyde production is continuous. Alternatively, the reactor 10 may also be operated at elevated pressures to further accelerate the reaction. Line 17 is connected to reactor 10 for removal of gas containing unreacted ethylene, any other reaction gases and/or pressure. Line 17 may vent the head space of the reactor 10. Line 17 may comprise a compressor, or other device as known to one skilled in the art, to compress gasses removed from the reactor 10. Additionally, line 17 re-circulates gases to the high shear device 40. Recycling the unreacted gases from reactor 10 may serve to further accelerate the reactions.

The high shear system is configured for single pass or multi-pass, wherein, after the initial mixing of the ethylene in reactor 10 and commencement of the process, the output from line 16 of reactor 10 goes directly to recovery of the acetaldehyde or to further processing. In some embodiments it may be desirable to pass the contents of reactor 10, or a liquid fraction containing unreacted ethylene, through the high shear device 40 during a second pass. In this case, the dispersion and the acetaldehyde product may be returned to pump input 21, pump 5, and/or high shear input 13, for further dispersion and reaction. Additional ethylene or catalyst may be injected into line 13, or it may be added directly into the high shear device (not shown), if needed.

In embodiments there may be several high shear devices 40 used in series. Two or more high shear devices 40 like high shear colloid devices are aligned in series, and are used to further enhance the reaction. Their operation may be in either batch or continuous mode. In some instances in which a single pass or "once through" process is desired, the use of multiple high shear devices 40 in series may also be advantageous. Multiple high shear devices are operated in series may permit the removal reactor 10 from the high shear system 100. In some embodiments, multiple high shear devices 40 are operated in parallel, and the outlet dispersions there from are introduced into one or more reactor 10.

The application of enhanced mixing of the reactants by high shear device 40 potentially causes greater conversion of ethylene to acetaldehyde in some embodiments of the process. Further, the enhanced mixing of the oxidant in the aqueous solution potentiates an increase in throughput of the process stream of the high shear system 100. In certain instances, the high shear device 40 is incorporated into an established process, thereby enabling an increase in production (i.e., greater throughput). In contrast to some existing methods that attempt to increase the degree of conversion of ethylene by increasing reactor pressures, the superior dissolution and/or emulsification provided by high shear mixing may allow in many cases a decrease in overall operating pressure while maintaining or even increasing reaction rate.

In embodiments, the method and system of this disclosure enable design of a smaller and/or less capital intensive process allowing selection of a reactor 10 having lower operating temperature and/or pressure capability than previously possible without the incorporation of high shear device 40. In embodiments, the disclosed method reduces operating costs/increases production from an existing process. Alternatively, the disclosed method may reduce capital costs for the design of new processes. Potential benefits of this modified system and method for the production of acetaldehyde include, but are not limited to, faster cycle times, increased throughput, reduced operating costs and/or reduced capital expense due to the possibility of designing smaller reactors and/or operating the acetaldehyde production at lower temperature and/or pressure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

We claim:

1. A method for producing acetaldehyde, comprising:
   forming an emulsion comprising oxidant gas bubbles dispersed in a pressurized aqueous solution wherein said oxidant gas bubbles have an average diameter of less than about 5 µm in a high shear device; and
   introducing said emulsion into a reactor comprising a catalyst and ethylene whereby acetaldehyde is produced.

2. The method of claim 1, wherein said pressurized aqueous solution is pressurized to at least about 203 kPa.

3. The method of claim 1 wherein said oxidant gas bubbles have an average diameter of less than about 1.5 µm.

4. The method of claim 1 wherein said high shear device has a nominal tip speed of at least about 5 m/s.

5. The method of claim 4 wherein said high shear device produces a localized pressure of about 1034 MPa at the tip.

6. The method of claim 1 further comprising enriching the oxidant gas with oxygen.

7. The method of claim 1 further comprising heating the dispersion prior to introduction into a reactor.

8. The method of claim 1 wherein forming said emulsion comprises subjecting said oxidant gas bubbles and pressurized aqueous solution to a shear rate of greater than about 20,000 $s^{-1}$.

9. The method of claim 1 wherein forming said emulsion comprises an energy expenditure of at least 1000 $W/m^3$.

10. The method of claim 1 wherein the catalyst comprises a fluidized bed catalyst or a fixed bed catalyst.

11. The method of claim 1 wherein the emulsion comprises a micro-foam.

* * * * *